US012790580B2

(12) United States Patent
Russom et al.

(10) Patent No.: US 12,790,580 B2
(45) Date of Patent: Nov. 10, 2026

(54) SELECTIVE LYSIS OF MAMMALIAN EUKARYOTIC CELLS AND VISUALIZATION OF VIABLE BACTERIAL CELLS

(71) Applicant: Aman Russom, Solna (SE)

(72) Inventors: Aman Russom, Solna (SE); Sharath Tippur Narayana Iyengar, Bandhagen (SE); Jiri Dietvorst, Antwerp (BE); Xavier Munoz Berbel, Barcelona (ES)

(73) Assignee: Aman Russom, Solna (SE)

( * ) Notice: Subject to any disclaimer, the term of this patent is extended or adjusted under 35 U.S.C. 154(b) by 312 days.

(21) Appl. No.: 18/562,266

(22) PCT Filed: May 18, 2022

(86) PCT No.: PCT/SE2022/050482
§ 371 (c)(1),
(2) Date: Nov. 17, 2023

(87) PCT Pub. No.: WO2022/245272
PCT Pub. Date: Nov. 24, 2022

(65) Prior Publication Data

US 2024/0240136 A1 Jul. 18, 2024

(30) Foreign Application Priority Data

May 19, 2021 (SE) .................................... 2150637-3

(51) Int. Cl.

| | |
|---|---|
| ***C12N 1/06*** | (2026.01) |
| ***C12N 1/02*** | (2006.01) |
| ***C12Q 1/04*** | (2006.01) |
| ***C12Q 1/18*** | (2006.01) |

(52) U.S. Cl.
CPC ................. *C12N 1/06* (2013.01); *C12N 1/02* (2013.01); *C12Q 1/04* (2013.01); *C12Q 1/18* (2013.01)

(58) Field of Classification Search
CPC ........................................................ C12N 1/06
See application file for complete search history.

(56) References Cited

U.S. PATENT DOCUMENTS

2010/0120085 A1* 5/2010 Hyman .................... C12Q 1/04
435/29
2015/0337362 A1 11/2015 Tarendeau

FOREIGN PATENT DOCUMENTS

EP 0571203 A1 11/1993
WO WO 2009/015484 A1 2/2009
WO WO-2019222862 A1 * 11/2019 ............... C12Q 1/04

OTHER PUBLICATIONS

Sidhu, G. S., and D. G. Oakenfull. "A mechanism for the hypocholesterolaemic activity of saponins." British journal of nutrition 55.3 (1986): 643-649. (Year: 1986).*
Maslova, V. A., and M. A. Kiselev. "Structure of sodium cholate micelles." Crystallography Reports 63.3 (2018): 472-475. (Year: 2018).*
Okazaki, Mitsuyo, et al. "Effect of phosphatidyl choline on the hemolytic activities of bile salts." Journal of Japan Oil Chemists' Society 29.10 (1980): 743-747. (Year: 1980).*
Mitra, Shuman, and Stephanie R. Dungan. "Cholesterol solubilization in aqueous micellar solutions of quillaja saponin, bile salts, or nonionic surfactants." Journal of agricultural and food chemistry 49.1 (2001): 384-394. (Year: 2001).*
Extended European Search Report issued in EP Application No. 22805076.1, mailed on Feb. 11, 2026.
Chang et al., "A rapid and sensitive colorimetric measurement of antibiotic efficacy against *Escherichia coli* in vitro", FEMS Microbiology Letters, 2016, 363(7): 1-6.
Domingues et al., "Solubilization of human erythrocyte membranes by ASB detergents", Brazilian Journal of Medical and Biological Research, 2008, 41: 758-764.
International Search Report and Written Opinion issued in International Application No. PCT/SE2022/050482, mailed on Jun. 17, 2022.
Iyengar et al., "Toward Rapid Detection of Viable Bacteria in Whole Blood for Early Sepsis Diagnostics and Susceptibility Testing", ACS Sensors, 2021, 6: 3357-3366.
Machen et al., "Same Day Identification and Full Panel Antimicrobial Susceptibility Testing of Bacteria from Positive Blood Culture Bottles Made Possible by a Combined Lysis-Filtration Method with MALDI-TOF VITEK Mass Spectrometry and the VITEK2 System", 2014, PLOS One, 9(2): 1-8.
Mitra et al., "Cholesterol solubilization in aqueous micellar solutions of Quillaja saponin, bile salts, or nonionic surfactants", J. Agric. Food Chem., 2001, 49: 384-394.
Zelenin et al., "Bacteria Isolation from Whole Blood for Sepsis Diagnostics", 15$^{th}$ International Conference on Miniaturized Systems for Chemistry and Life Sciences, Oct. 2-6, 2011, pp. 518-520.
Javaloyas et al., "Epidemiology and Prognosis of Bacteremia: A 10-y Study in a Community Hospital", Scandinavian Journal of Infectious Diseases, 2002, vol. 34, No. 6, pp. 436-441.
Seymour et al., "Assessment of Clinical Criteria for Sepsis For the Third International Consensus Definitions for Sepsis and Septic Shock (Sepsis-3)", JAMA, 2016, vol. 315, No. 8, pp. 762-774.
Yagupsky et al., "Quantitative Aspects of Septicemia", Clinical Microbiology Reviews, Jul. 1990, vol. 3, No. 3, pp. 269-279.
Kumar et al., "Best evidence in critical care medicine; Early antibiotics and survival from septic shock: it's about time", Can J Anesth, 2006, vol. 53, No. 11, pp. 1157-1160.

(Continued)

*Primary Examiner* — Robert J Yamasaki
(74) *Attorney, Agent, or Firm* — Knobbe, Martens, Olson & Bear, LLP

(57) ABSTRACT

A lysis buffer includes saponin and cholate. A method for selectively lysing mammalian eukaryotic cells in a liquid sample including mammalian eukaryotic cells and other microorganisms uses the lysis buffer. A visualization buffer includes ferric cyanide and/or ferrocyanide and ferric citrate. A method for visualization of viable bacterial cells through formation of Prussian blue uses the visualization buffer.

6 Claims, 5 Drawing Sheets

(56) References Cited

OTHER PUBLICATIONS

Frank et al., "Controlled Clinical Comparison of Three Commercial Blood Culture Systems", Eur J Clin Microbiol Infect Dis, 1999, vol. 18, pp. 248-255.
Sage et al., "Rapid Visual Detection of Microorganisms in Blood Culture", Journal of Clinical Microbiology, Jul. 1984, vol. 20, No. 1, pp. 5-8.
Haimi-Cohen et al., "Initial Concentration of *Staphylococcus epidermidis* in Simulated Pediatric Blood Cultures Correlates with Time to Positive Results with the Automated, Continuously Monitored BACTEC Blood Culture System", Journal of Clinical Microbiology, Mar. 2002, vol. 40, No. 3, pp. 898-901.
Sinha et al., "Emerging Technologies for Molecular Diagnosis of Sepsis", Clinical Microbiology Reviews, Apr. 2018, vol. 31, No. 2, pp. 1-26.
Hosokawa et al., "Leukocyte Counting From a Small Amount of Whole Blood Using a Size-Controlled Microcavity Array", Biotechnology and Bioengineering, Aug. 2012, vol. 109, No. 8, pp. 2017-2024.
Barr et al., "ISCOMs and other saponin based adjuvants", Advanced Drug Delivery Reviews 32, 1998, pp. 247-271.
Zhao et al., "Dioscin, a natural steroid saponin, shows remarkable protective effect against acetaminophen-induced liver damage in vitro and in vivo", Toxicology Letters, 2012, vol. 214, pp. 69-80.
Schubert et al., "Structural Changes in Membranes of Large Unilamellar Vesicles after Binding of Sodium Cholate", Biochemistry, 1986, vol. 25, No. 18, pp. 5263-5269.
Albalak et al., "Effects of Submicellar Bile Salt Concentrations on Biological Membrane Permeability to Low Molecular Weight Non-Ionic Solutes", Biochemistry, 1996, vol. 35, No. 24, pp. 7936-7945.
Ravnikar et al., "Chemoporation using saponins or cholates: an alternative method for transformation of bacterial cells", Biotechnology Letters, 2009, vol. 31, pp. 1943-1946.
Arendrup et al., "How to interpret MICs of antifungal compounds according to the revised clinical breakpoints v. 10.0 European committee on antimicrobial susceptibility testing (EUCAST)", Clinical Microbiology and Infection, 2020, vol. 26, pp. 1464-1472.

* cited by examiner

SELECTIVE LYSIS OF MAMMALIAN EUKARYOTIC CELLS AND VISUALIZATION OF VIABLE BACTERIAL CELLS

TECHNICAL FIELD

The present disclosure relates to a lysis buffer and a method for selectively lysing mammalian eukaryotic cells in a liquid sample comprising mammalian eukaryotic cells and possibly microorganisms. It also relates to a visualization buffer and method for visualization of viable bacterial cells through formation of Prussian blue, and to a method for bacterial antibiotic susceptibility testing.

BACKGROUND ART

Sepsis is a serious medical condition characterized by a whole-body inflammatory state caused by blood stream infection. *Escherichia coli* (*E. coli*) is a gram negative bacteria, which today is one of the most leading causes of blood stream infections [1]. In sepsis, bacteria reach the blood stream from a local region of infection and spread in the body, leading to organ dysfunction and death of the patient [2]. According to 2018 statistics from the World Health Organization (WHO), about 30 million people are affected by sepsis worldwide, including 3 million new-born kids and 1.2 million children. 6 million people die of sepsis in the world every year, 500 thousand of them new-born kids, and this condition is also responsible of 1 in 10 maternal deaths. The high mortality is mostly associated with the difficulty of diagnosing sepsis at its early stages: initial bacterial concentrations do not exceed 100 colony forming units (CFU)/mL [3] and every hour of delay in the diagnostic and treatment increases the mortality of patients up to 10% [4].

The fast diagnostic requirements are not attainable with traditional golden standards, i.e. cell culture and Polymerase Chain Reaction (PCR) amplification methods, which require between 24 to 72 h before appropriate antibiotics can be prescribed to the patients [5-7]. Better performances are obtained with sepsis diagnosis kits currently available on the market, e.g. IRIDICA, SeptiFast, SeptiTest or U-dHRM. These kits combine lysis buffers for fast blood sample pre-treatment and DNA extraction, with PCR analysis enabling the detection of bacterial DNA, and thus diagnosing sepsis within 4 to 8 hours. Main limitations of these kits are the low sensitivity and specificity due to background signal from human DNA and the impossibility to distinguish between DNA coming from live or dead bacteria [8]. Moreover, since bacteria are lysed to extract DNA, it is not possible to perform antimicrobial susceptibility tests and medical prescriptions are based on genetic information, e.g. the presence of resistance genes.

Although some technologies for viable bacteria isolation are now being developed based on micro-filtration, they suffer from blood clogging and low throughput [9]. Thus, there is an urgent need for faster and more efficient methods for viable bacteria isolation and detection, which may be used is sepsis diagnosis and in defining sepsis treatment.

SUMMARY OF THE INVENTION

It is an object of the present invention to provide a lysis buffer and method for selectively lysing mammalian eukaryotic cells in a liquid sample comprising mammalian eukaryotic cells and possibly microorganisms. It is also an object to provide a visualization buffer and method for visualization of viable bacterial cells through photo-catalytic formation of Prussian blue. It is further an object to provide a method for bacterial antibiotic susceptibility testing. These buffers and methods provide a faster and more efficient isolation of microorganisms and detection of viable bacterial cells than known methods.

According to a first aspect there is provided a lysis buffer for selectively lysing mammalian eukaryotic cells in a liquid sample comprising mammalian eukaryotic cells and possibly microorganisms, the lysis buffer comprising saponin and cholate in a concentration ratio (w/v) of 1:5 to 10:1.

The liquid sample comprising mammalian eukaryotic cells and possibly microorganisms may be a blood sample, such as a whole blood sample from mammals such as humans, or other bodily fluids such as urine. Alternatively, the liquid sample may be a liquid food sample or liquidised food sample or a beverage sample, comprising mammalian eukaryotic cells.

That the mammalian eukaryotic cells are lysed is meant that the membranes of the cells are broken down.

The microorganisms may include prokaryotic cells such as bacteria (gram positive bacteria (such as *Staphylococcus*) or gram negative bacteria (such as *E. coli*)) and archaea, with a typical size range of 0.5 to 5 μm in diameter. The microorganisms may alternatively be eukaryotic microbes such as fungi, protozoa and algae. In yet an example, the microorganism may be a virus. In one alternative, the liquid sample comprises two or more of the mentioned microorganisms.

The buffer may comprise a solution that may for example be water or a phosphate buffer, such as 1×PBS (phosphate buffer saline)—a water-based salt solution containing disodium hydrogen phosphate, sodium chloride and, in some formulations, potassium chloride and potassium dihydrogen phosphate. Other buffers or solutions known in the art are also possible such as LB (Luria-Bertani broth), MH (Muller Hilton broth) and other nutrient broths. The buffer helps to maintain a constant pH or can be made to achieve the required pH by adding suitable acid or base. The pH of the lysis buffer may be about 6-7, or 6.5.

Saponin and cholate are completely dissolved in the solution to form the lysis buffer.

The cholate may be sodium cholate. Cholate being a salt or ester of cholic acid.

Sodium cholate is a cholate salt and an organic sodium salt.

It is known from prior art that sodium cholate can be used to kill bacterial cells.

Sodium cholate hydrates are bile salts produced from cholesterol in the liver, whose interaction with the biomembranes is extensively studied, but their effect is still not understood well [12-14]. Ravnikar, M., et al. showed an effective plasmid transformation to competent bacterial cells using cholates [14].

Saponin, also known as triterpene glycosides, is commonly found in plants and used to treat several diseases such as malignancy. Saponin is also known to cause suicidal erythrocyte death [10, 11].

Different lysis buffers are used for DNA and RNA extraction from both blood and bacteria. Among them, saponin is known to cause suicidal erythrocyte death [10, 11]. There are various other lysis buffer such as TRITON X-100, Tween-20, Tween-80 or any other Tween combination also used as lysis buffers and which ruptures both blood cells and bacteria.

The above described lysis buffer comprises saponin and cholate in a concentration ratio (w/v) of saponin to cholate of 1:5 to 10:1, or 1:4 to 10:1, or 1:3 to 10:1, or 1:2 to 10:1, or 1:1 to 10:1, or 2:1 to 10:1, or 3:1 to 10:1, or 4:1 to 10:1, or 5:1 to 10:1, or 6:1 to 10:1, or 7:1 to 10:1, or 8:1 to 10:1, or 9:1 to 10:1, or 1:5 to 9:1, or 1:5 to 8:1, or 1:5 to 7:1, or 1:5 to 6:1, or 1:5 to 5:1, or 1:5 to 4:1, or 1:5 to 3:1, or 1:5 to 2:1, or 1:5 to 1:1, or 1:5 to 1:2, or 1:5 to 1:3, or 1:5 to 1:4, or 1:3 to 1:1, or 1:1 to 3:1, or 3:1 to 5:1, or 5:1 to 8:1, or 8:1 to 10:1.

The lysis buffer show complete, or almost complete, rupture of mammalian eukaryotic cells while keeping up to 100% of the microorganisms viable in the liquid sample up to 1 hour of lysis buffer exposure when mixed with the sample such that a concentration of saponin and cholate in the sample is 0.6-20% (w/v) and 1-8% (w/v), respectively. This has not been demonstrated with known lysis buffers. With this lysis buffer there is no killing of microorganisms, only mammalian eukaryotic cells, and the microorganisms are kept viable in the sample treated with the lysis buffer. Both gram positive and gram negative bacteria are viable after lysis buffer treatment.

The saponin concentration in the liquid sample can be up to 20% (w/v) without affecting *E. coli* viability in the liquid sample. The concentration of saponin in the liquid sample may be 0.6-20%, 0.6-15%, 0.6-10%, 0.6-5% or 0.6-3% or 0.6-2% (w/v).

The cholate concentration in the liquid sample can be up to 8% in the final mix. There is ~50% loss in *E. coli* viability with 8% cholate concentration. The cholate concentration may be 1-8%, 1-6%-1-4%, 1-3% or 1-2% (w/v) in the liquid sample.

Saponin alone as lysis buffer does not rupture 100% of all blood cells, even after 1 hr of exposure and they form blood clumps sometimes.

Sodium cholate alone as lysis buffer, on the other hand ruptures all the blood cells in around 110s.

Saponin alone does not affect bacterial viability (for both gram negative (*E. coli*) and gram positive (Staph).

On the other hand, sodium cholate kills 43% of gram negative bacteria within 1 hr but does not affect the viability of gram positive bacteria.

By mixing saponin and sodium cholate together, the viability of gram negative bacteria can be retained. Blood cells can be ruptured faster (that is in 100s). So there is a win-win situation on both mammalian eukaryotic and bacteria sides.

If the liquid sample is a blood sample, white and red blood cells and blood platelets are destroyed, getting ruptured, while microorganisms, such as prokaryotic cells, are kept viable. There is further no clump formation, aggregation, of ruptured cells in the lysis buffer treated sample. The remainders of the ruptured blood cells in the treated sample have a smaller size than the size of viable prokaryotic cells, e.g. less than 0.45 μm.

The lysis buffer combines two reagents for selectively lysing mammalian eukaryotic cells in a mixture comprising mammalian eukaryotic and microorganisms. With the present lysis buffer fast and efficient rupture of mammalian eukaryotic cells is obtained, while keeping microorganisms viable, thereby there is selective rupturing of cells from a heterogeneous cell population in a sample.

The lysis buffer was engineered to ensure fast and efficient disruption of the plasmatic membrane of mammalian eukaryotic cells, while preserving the integrity and viability of microorganisms.

Once the liquid sample has been treated with the lysis buffer and the mammalian eukaryotic cells killed off, the liquid sample and its possible content of viable microorganisms can be analysed in various downstream analyses. The viable microorganisms may be separated from other components in the lysis buffer treated sample (such as remainders of ruptured mammalian eukaryotic cells) before such further analysis.

Saponin may be present in the lysis buffer in a concentration of 0.6-80% (w/v) and cholate may be present in the lysis buffer in a concentration of 1-40% (w/v).

Percentage of saponin and cholate is calculated based on weight (in grams) per unit volume (mL) (w/v). 1% saponin means 1 g of saponin powder in 100 mL solution. 2% sodium cholate means 2 g of sodium cholate powder in 100 ml solution.

A saponin solution and a cholate solution may be prepared separately and thereafter mixed to form the final lysis buffer.

According to a second aspect there is provided a method of selectively lysing mammalian eukaryotic cells in a liquid sample comprising mammalian eukaryotic cells and possibly microorganisms, the method comprising: adding to a volume of a liquid sample comprising mammalian eukaryotic cells and possibly microorganisms the lysis buffer described above such that concentrations of saponin and cholate in the formed mixture is 0.6-20% (w/v) and 1-8% (w/v), respectively, and to incubate the mixture, thereby lysing mammalian eukaryotic cells in the mixture.

The method may be used for liquid samples from where there is a need to separate and detect viable microorganisms, such as bacterial s cells and fungi, from mammalian eukaryotic cells.

The method may be suitable e.g. for early sepsis diagnosis as it leaves only the bacterial cells and/or fungi intact in the sample.

If the liquid sample is a blood sample, no pre-treatment of the blood sample before mixing with lysis buffer is necessary. The blood sample may be mixed with the lysis buffer immediately after being collected. Alternatively, the blood sample may be stored for a period of time (such as at 4° C. for up to 2 days or until blood cells agglomerate, whichever happens first) and thereafter mixed with the lysis buffer.

The step of allowing the lysis buffer to react with the liquid sample, the incubation step, may comprise a step of stirring the mixture.

The incubation time may be as little at 100 seconds or more. The incubation time should allow enough time for the mammalian eukaryotic cells in the liquid sample to rupture. Longer incubation times, such as 10 minutes or more may be used, such as 10 minutes to 60 minutes, or 60 minutes to 8 hours, or 2 hours to 10 hours.

The incubation may take place at room temperature or at a higher temperature below 65° C., or up to 37° C.

Once the liquid sample has been treated with the lysis buffer and the mammalian eukaryotic cells lysed, the liquid sample and its possible content of viable microorganisms can be analysed in various downstream analyses. The viable microorganisms may be separated from other components in the lysis buffer treated sample (such as remainders of ruptured mammalian eukaryotic cells) before such further analysis. For example may genotypic analysis of the microorganisms be used after DNA extraction and amplification of the DNA through e.g. PCR, isothermal amplification, DNA bar coding, nanopore sequencing. Alternatively, phenotypic analysis of bacterial colonies may be performed, such as colorimetric based detection or continuous bacterial growth monitoring using microbioreactor, standard agar plating, standard plate based or solution or plating based antibiotic susceptibility testing, optical density measurement using spectrophotometer, among others.

According to a third aspect there is provided a method of separating an enriching microorganisms, wherein the method comprises the method described above and further steps of, after the incubation step, separating possible micro-organisms from other components in a volume of the liquid sample and enriching the microorganisms.

The separation can be performed by passing the volume of the liquid sample through a filter having a pore size smaller than an average diameter of a microorganism of interest, such that microorganisms are captured on/in the filter. Through such a filtration lysed mammalian eukaryotic cells are removed and microorganisms, such as bacterial cells may be enriched. The filtering may be performed by passing the liquid sample with lysed mammalian cells by means of a syringe through a filter paper. Such filter paper may be made of cellulose or nitrocellulose or PET or PTFE, or any other filter papers and/or glass-fibre and/or plastic array filter, and/or silicon-based or glass based material with the pore size ranging from 0.2 μm to 0.5 μm. Alternative, other size based enrichment systems can be used such as microfluidics based on active or passive systems or immunoassays or any other conventional or emerging technologies.

According to a fourth aspect there is provided a visualization buffer for visualization of viable bacterial cells through photo-catalytic formation of Prussian blue, the visualization buffer comprising ferric cyanide and/or ferrocyanide and ferric citrates, wherein a concentration of ferric cyanide and/or ferrocyanide in the visualization buffer is 0.5 mM to 4.5 mM and a concentration of ferric citrate is 2 mM to 9 mM.

When a sample possibly comprising viable bacterial cells is incubated in the visualization buffer during continuous irradiation with catalytic light in the range between 400 and 800 nm, viable bacterial cells metabolically reduce iron (III) complexes, initiating a photo-catalytic cascade toward Prussian Blue formation over time.

The visualization solution comprises a combination of two iron donors. One iron donor is ferric cyanide and/or ferrocyanide and the second donor is ferric citrate.

The concentration of ferric cyanide and/or ferrocyanide in the solution is 0.5 mM to 4.5 mM, or 0.5 mM to 4 mM, or 0.5 mM to 3.5 mM, or 0.5 mM to 3 mM, or 0.5 mM to 2.5 mM, or 0.5 mM to 2 mM or 0.5 mM to 1.5 mM or 0.5 mM to 1 mM, or 1 mM to 4.5 mM, or 1.5 mM to 4.5 mM, or 2 mM to 4.5 mM, or 2.5 mM to 4.5 mM, 3 mM to 4.5 mM, or 3.5 to 4.5 mM, or 4 to 4.5 mM, or 0.6 mM to 2.5 mM, or 1 mM to 2 mM, or 2 mM to 4 mM. A concentration of ferric citrate is 2 mM to 9 mM, or 2 mM to 8.5 mM, or 2 mM to 8 mM, or 2 mM to 7.5 mM, or 2 mM to 7.0 mM, or 2 mM to 6.5 mM, or 2 mM to 6.0 mM, or 2 mM to 5.5 mM, or 2 mM to 5.0 mM, or 2 mM to 4.5 mM, or 2 mM to 4.0 mM, or 2 mM to 3.5 mM, or 2 mM to 3.0 mM, or 2 mM to 2.5 mM, or 2.5 mM to 9 mM, or 3 mM to 9 mM, or 3.5 mM to 9 mM, or 3.5 mM to 9 mM, or 4 mM to 9 mM, or 4.5 mM to 9 mM, or 5 mM to 9 mM, or 5.5 mM to 9 mM, or 6 mM to 9 mM, or 6.5 mM to 9 mM, or 7 mM to 9 mM, or 7.5 mM to 9 mM, or 8 mM to 9 mM, or 8.5 mM to 9 mM, or 1 mM to 6 mM.

The ratio of ferric cyanide and/or ferrocyanide to ferric citrate is 0.06 to 2.25, or 0.1 to 2, or 0.2 to 1.5.

The visualization buffer may, as stated above, comprise the combination of ferric cyanide with ferric citrate, and/or ferrocyanide with ferric citrate. Ferric cyanide and ferrocyanide can be interchanged and will depend on the same concentrations and ratios as mentioned before, and will provide the same amount of Prussian blue.

The solution may be water or for example be a phosphate buffer, such as 1×PBS (phosphate buffer saline)—a water-based salt solution containing disodium hydrogen phosphate, sodium chloride and, in some formulations, potassium chloride and potassium dihydrogen phosphate. Other solutions and buffers known in the art are also possible, such as bacterial nutrient media such as LB, MH broth or any other broth which can be made up to the desired pH. The buffer helps to maintain a constant pH. The pH may be about 6-7, or 6.5. The ferric cyanide and the ferric citrate are completely dissolved in the solution.

Viable bacterial cells metabolically reduce iron (III) complexes, initiating a photo-catalytic cascade toward Prussian Blue formation over time when the solution is continuously irradiated with visible light in the range between 400 and 800 nm. Prussian Blue formation is an indirect method to detect the metabolism of bacteria. The combination of these precursors is referred collectively as a PB solution as they form Prussian blue colour, an intense blue colour detectable with the bare eye.

The coupling of the ferric ammonium citrate to ferricyanide is widely reported and dates back to 1842, with the discovery of cyanotype, a photographic printing process. The process and the reaction was later improved for the development of blueprints. Ferric ammonium citrate is photosensitive and reacts with UV, or at a slower rate, with blue visible light. In this case, the ferric iron is reduced and reacts with the ferricyanide, resulting in the formation of Prussian Blue.

When the above describe visualization buffer is used to visualize viable bacterial cells, a modified version of the cyanotyping is used, where the formation of Prussian blue is coupled to bacterial cell metabolism through a photo-catalytic approach. The starting iron donors are potassium ferricyanide and ferric ammonium citrate, both used at specific concentrations.

This reduced form cannot spontaneously react with the provided ferric ammonium citrate. The bond between the iron and the citrate cannot be spontaneously broken by the presence of ferrocyanide. Visible light illumination in the range between 380 and 450 nm provided by an artificial light source is still not energetic enough to release free iron ions from citrate, but it requires the presence of living bacteria to activate these molecules and initiate the photo-metabolic-catalytic reaction resulting in the Prussian blue formation and the appearance of an intense blue colour detectable with the bare eye.

Furthermore, at the provided conditions, the ferric citrate does not spontaneously reduce to iron (II) citrate, preventing the formation of Prussian blue in the absence of prokaryotic cells.

With a citrate concentration of 2.5 mM, ferricyanide becomes toxic from concentrations 1.25 mM and above. With a citrate concentration of 5 mM, ferricyanide becomes toxic from concentrations 2.5 mM and above. This trend continues, with the citrate concentration requiring at least double the ferricyanide concentration, to counteract the toxicity, up until 20 mM where the toxicity is too high.

Citrate is not toxic to bacteria, even at 40 mM no negative effects on growth can be observed. The limitation of increasing the citrate concentration is the auto formation of Prussian blue. This means that, from a concentration of 10 mM of citrate or higher, with any cyanide concentration Prussian blue will be formed without bacteria. At lower concentrations, bacterial presence is crucial for Prussian blue formation.

According to a fifth aspect there is provided a method of visualizing viable bacterial cells in/on a sample, the method comprising: incubating a sample possibly comprising viable bacterial cells in the visualization buffer described above during illumination, thereby allowing Prussian blue formation, wherein presence of Prussian blue correlates to presence of viable bacterial cells in/on the sample.

The sample may be a solution comprising viable bacterial cells. The sample may have been pre-treated by separating any (viable) bacterial cell from other components in the liquid sample before incubating in the visualization buffer. The sample may have been pre-treated with the lysis buffer discussed above to lyse any mammalian eukaryotic cells in the sample, possibly followed by a separation step and enrichment step, before incubation in the visualization buffer. When incubating such a sample in the visualization buffer, the buffer is added to the sample such that a concentration of ferric cyanide and/or ferrocyanide in the solution is 0.5 mM to 4 mM and a concentration of ferric citrate is 2 mM to 8 mM. The incubation step may also comprise a step of mixing or stirring.

Alternatively, the sample may by a filter or similar on/in which the viable prokaryotic cells are present. The filter with prokaryotic cells being immersed in the visualization buffer. The solution comprising viable prokaryotic cells may have been pressed through a filter or similar, such that prokaryotic cells are captured in/on the filter and smaller components of the sample removed by passing through the filter.

The incubation time is dependent on the number of viable prokaryotic cells in/on the sample. The incubation time (in the presence of illumination) could for example range from a couple of hours up to 24 hours depending on sample. The incubation may take place at RT up to 37° C.

Illumination of the sample mixed with or immersed in the visualization buffer may be provided by the use of an artificial light source. The light used may have a wavelength of 400-800 nm (visible light). An optimal single wavelength light may be in the range of 350-400 nm. Wavelengths below 400 nm can, however, be detrimental for bacterial viability.

Thereby the iron molecules uncouple from the citrate, freeing it up for Prussian blue formation, as discussed above.

Thereby, a colorimetric method based on Prussian blue colour formation for detecting viable bacterial cells colorimetrically is presented.

Finally, since the reaction needs both viable bacterial cells and a light source, the exact onset of Prussian blue formation can be perfectly controlled.

By using a reference sample with known bacterial cell concentration or by comparing the Prussian blue intensity with a reference curve it may be possible to determine an approximate concentration of viable bacterial cells in a sample.

Providing a sample possibly comprising viable bacterial cells may be prepared by separating possible bacterial cells from other components in a volume of a liquid of the sample by passing the volume of the liquid sample through a filter having a pore size smaller than an average diameter of the bacterial cells, such that bacterial cells are captured on/in the filter, and when incubating the sample in the visualization buffer, the filter is immersed in the visualization buffer.

The filter with captured bacterial cells therein/thereon is immersed in the visualization buffer, thereby allowing Prussian blue formation when illuminating the filter immersed in the visualization buffer. Thereby, visible detection of Prussian blue formation, which correlates to presence of viable bacterial cells in/on the filter, is possible.

Filtering can be performed by using a filter paper, which may be of nitrocellulose or PTFE material or any other hydrophilic membrane based filters. Alternatively, instead of a filter any surface, non-toxic to microorganisms, where bacterial cells can be captured can be used.

The pore size of the filter paper can be anything smaller than an average diameter of bacterial cells, such as about 0.45 μm or smaller.

For phenotypic detection of bacterial cells captured on the filter paper, the filter paper is dipped in the visualization buffer, forming Prussian blue in the presence of light. The presence of bacterial cells is confirmed by the photo-catalytic reaction where a blue colour formation can be observed on the filter paper, and also in the solution in which the filter paper is dipped (because bacteria also proliferate in the solution over time).

According to a sixth aspect there is provided a method of selectively lysing mammalian eukaryotic cells in a liquid sample comprising mammalian eukaryotic cells and possibly bacterial cells, and thereafter visualizing any viable bacterial cells, the method comprising the method of selectively lysing mammalian eukaryotic cells as described above followed by the method of visualizing viable bacterial cells in/on a sample as described above.

Hence, it is clear that the methods of selectively lysing mammalian eukaryotic cells in a liquid sample comprising mammalian eukaryotic cells and possibly microorganisms, and the method of visualizing viable bacterial cells, can be used in sequence as a combined method. An area of use of such a combined method could be for sepsis identification (when the microorganism is a bacterium). The visualization method benefitting from the selective lysis of mammalian eukaryotic cells, keeping bacterial cells viable and intact. Alternatively, the methods may be used in isolation from each other.

According to a seventh aspect there is provided a method for bacterial antibiotic susceptibility testing, the method comprising: dividing a volume of a liquid sample comprising mammalian eukaryotic cells and possibly bacterial cells in a test volume and a reference volume, adding an antibiotic to the test volume and adding the lysis buffer described above to the reference volume and to the test volume, respectively, such that concentrations of saponin and cholate in the formed mixtures is 0.6-20% (w/v) and 1-8% (w/v), respectively, and incubating the mixtures, thereby lysing mammalian eukaryotic cells in the mixture. Thereafter bacterial cells are isolated from the respective mixtures in/on a test sample and in/on a reference sample, respectively, and the reference sample is incubated in the visualization buffer described above during illumination, and the test sample is incubated in the visualization buffer described above in presence of an antibiotic during illumination, thereby allowing Prussian blue formation, wherein presence of Prussian blue correlates to presence of viable bacterial cells in/on the test and reference samples, respectively, and Prussian blue intensity from the test sample and the reference sample are compared.

If there is a difference in Prussian blue intensity when comparing the test and reference samples this indicates that the antibiotic has an effect on the viability of bacterial cells in the sample. Such information can be useful for identifying which antibiotic to use when treating a bacterial blood infection, such as sepsis.

Since the method preserves bacterial cell integrity and activity, it also allows susceptibility testing and the detection of live bacterial cells.

The antibiotic may be added directly into the visualization buffer. The test sample may be incubated with the antibiotic for 30 minutes or more during illumination to allow time for the antibiotic to act on the viable bacterial cells. Thereafter the number of living bacterial cells is measured through the formation of Prussian blue. Susceptible bacterial cells die after incubation with the antibiotic and there is no colour development. On the contrary, resistant bacterial cells remain metabolically active and start the photo-catalytic cascade and the corresponding blue colour formation.

The amount of antibiotic, such as ampicillin, added may be such that the concentration in the mixture is 1-8 mg/mL.

Any antibiotics such as gentamicin, ciprofloxacin or any other antibiotics can be added in different concentration ranges to determine the microbial contamination depending on the microorganism of interest.

According to a sixth aspect there is provided a kit for selectively lysing mammalian eukaryotic cells in a liquid sample comprising mammalian eukaryotic cells and possibly bacterial cells, and thereafter visualizing viable bacterial cells, comprising the lysis buffer above and the visualization buffer above.

The kit may further comprise a filter having a pore size smaller than an average diameter of bacterial cells.

The bacterial cells may have a typical size range of 0.5 to 5 μm in diameter and the pore size may be less than 0.45 μm.

In the methods described above, the liquid sample may be selected from a blood sample, urine, beverage, water, liquid or liquidized food sample.

Urine samples may be tested for urinary tract infection. Respiratory tract infection may be tested from swabs or sputum. Microbial contamination of food or beverage may be detected by the methods above. It is to be understood that the lysis buffer only is used on liquid samples comprising mammalian eukaryotic cells. If there are no mammalian eukaryotic cells in a sample, treatment with the lysis buffer is of course not necessary.

Figure 2A:
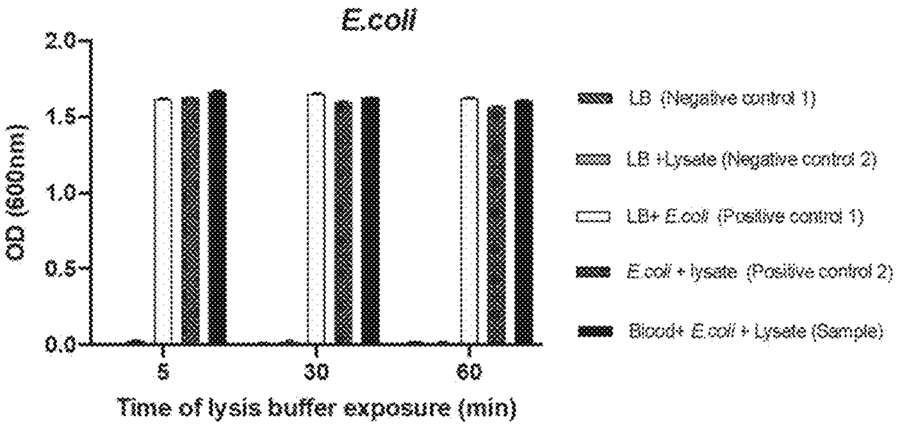
Figure 2B:
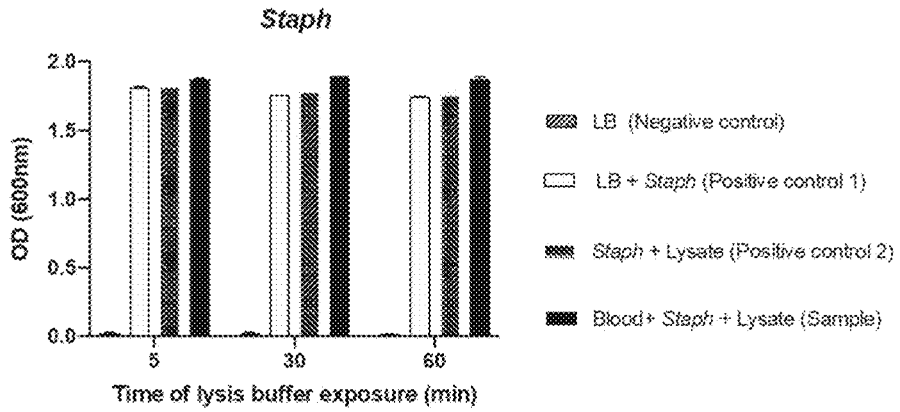

In FIG. 2*a* and FIG. 2*b* is shown the effect of lysis buffer on viability of *E. coli* and Staph, respectively.

Figure 3:
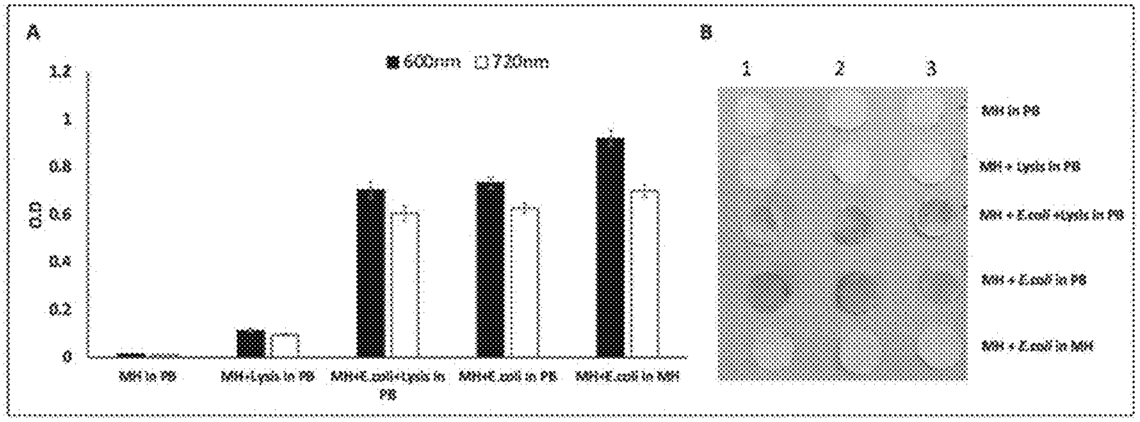

FIG. 3 shows Prussian blue based detection of *E. coli* spiked Mueller-Hinton (MH) media on filter paper. In A) is shown OD-values and in B) Prussian blue formation.

Figure 4:
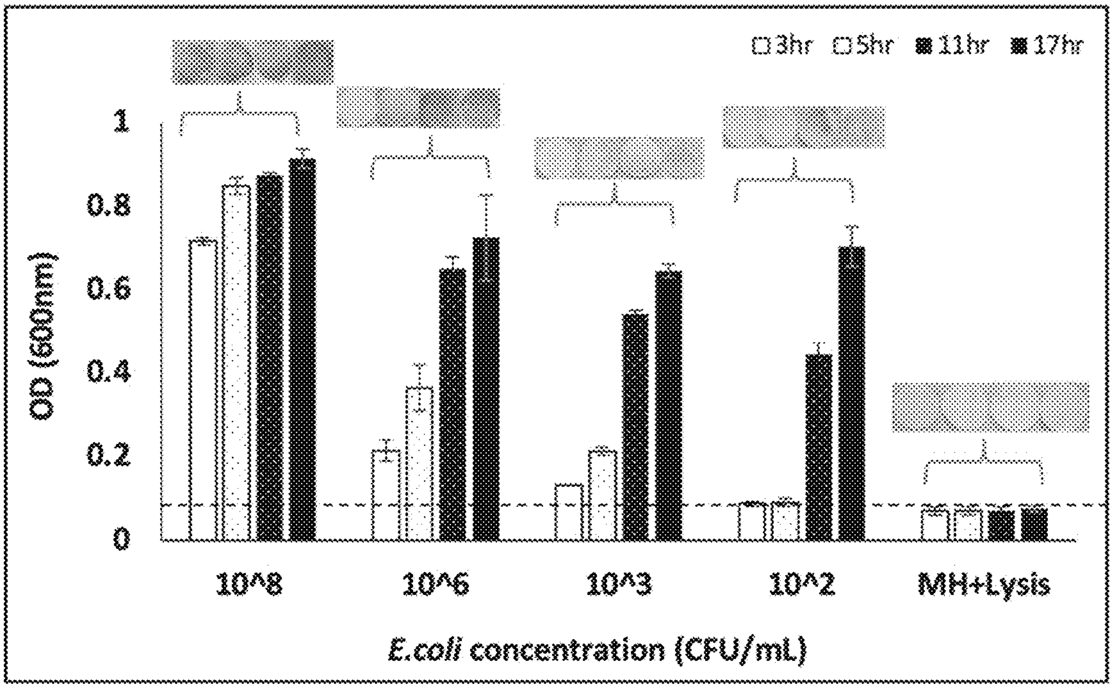

FIG. 4 shows time needed for bacteria detection using Prussian blue formation.

Figure 5:
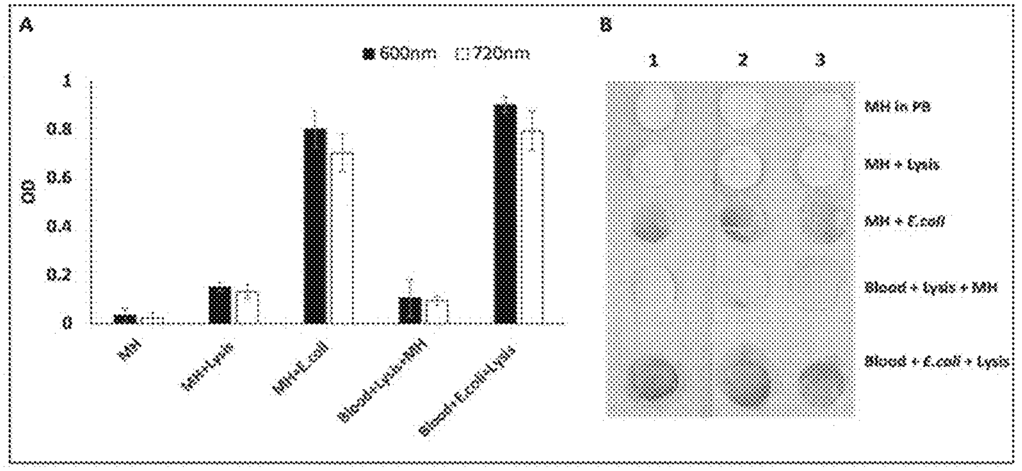

FIG. 5 shows detection of *E. coli* spiked in whole blood. In A) is shown OD-values and in B) Prussian blue formation.

Figure 6:
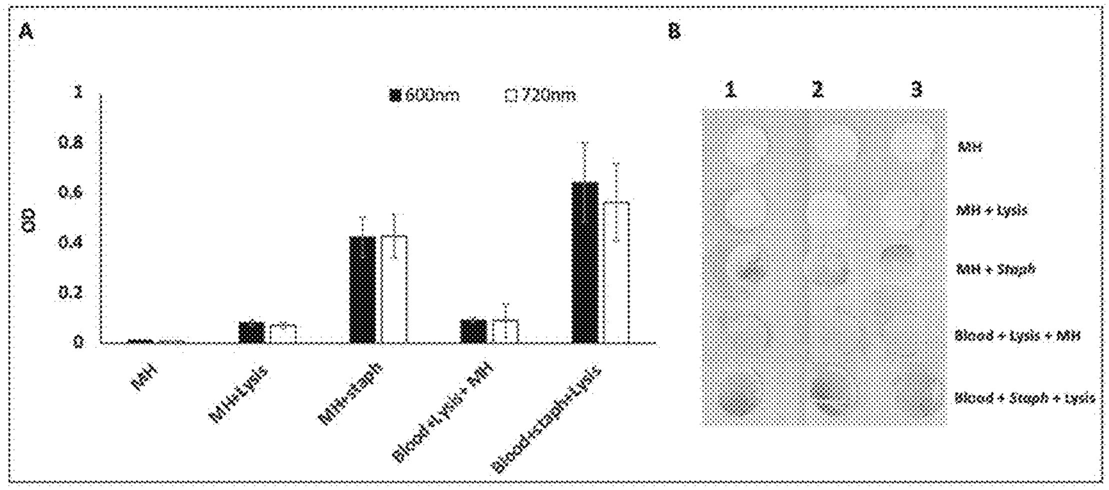

FIG. 6 shows detection of Staph spiked in whole blood. In A) is shown OD-values and in B) Prussian blue formation.

Figure 7:
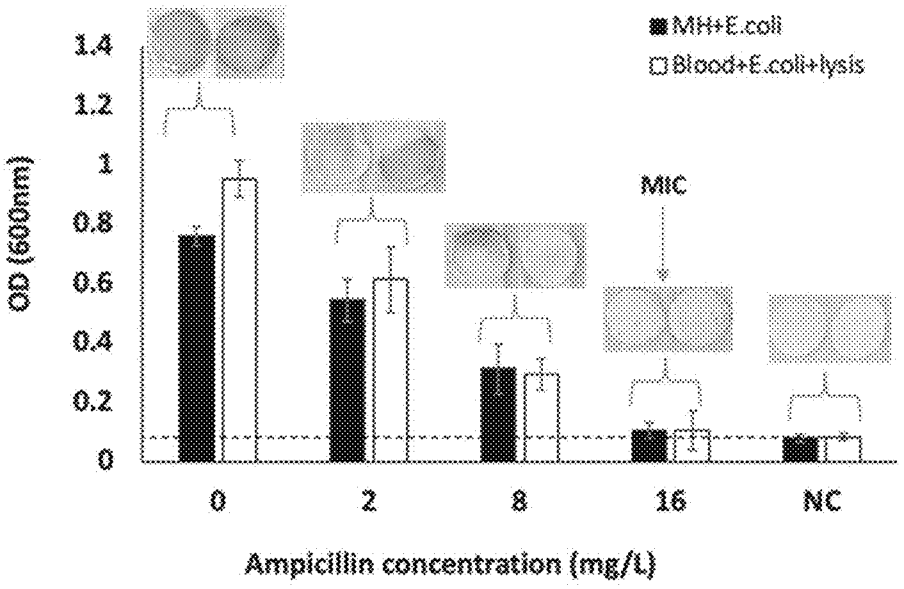

FIG. 7 shows antibiotic susceptibility testing using different concentrations of ampicillin on *E. coli* spiked in blood and in MH media.

Figure 8:
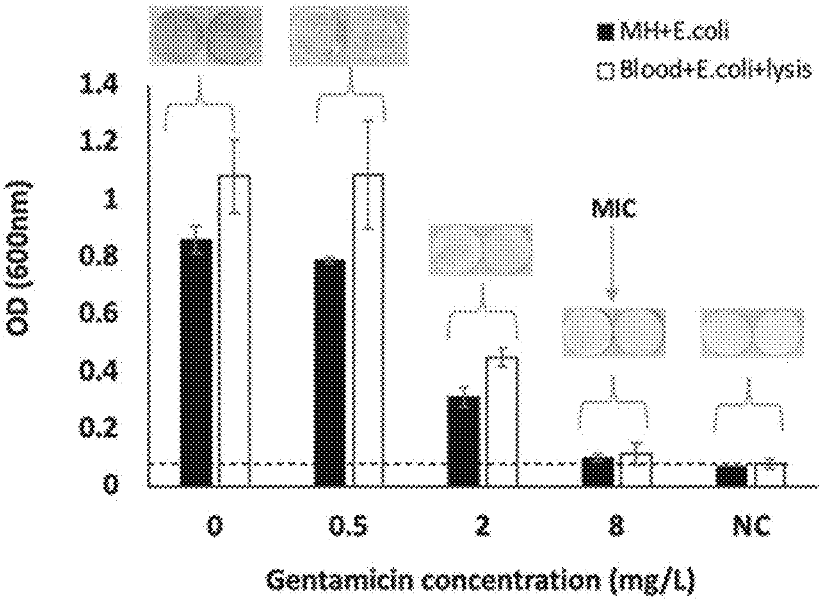

FIG. 8 shows antibiotic susceptibility testing using different concentrations of gentamicin on *E. coli* spiked in blood and in MH media.

DETAILED DESCRIPTION

Figure 1:
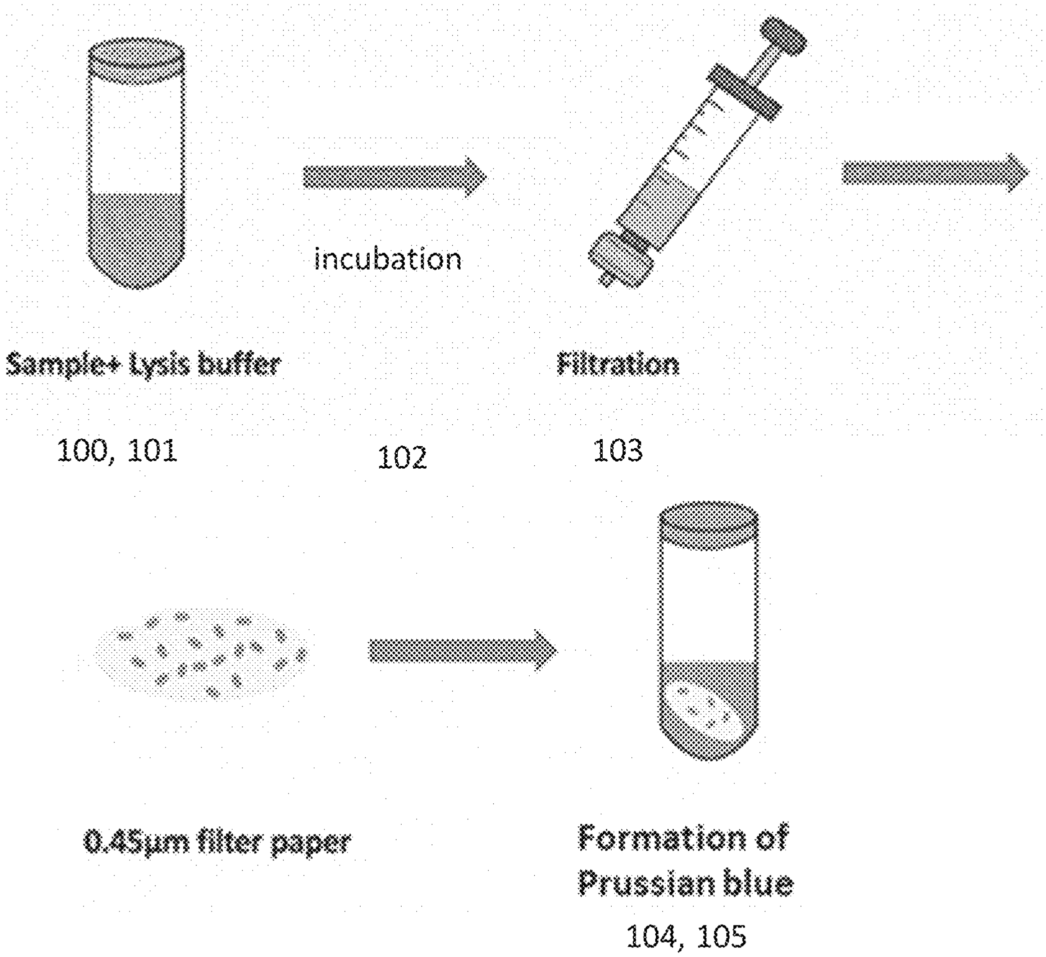
FIG. 1 schematically shows a method of selectively lysing mammalian eukaryotic cells in a liquid sample comprising mammalian eukaryotic cells and possibly microorganisms such as bacterial cells. In the method a lysis buffer is used, which disrupts mammalian eukaryotic cells and keeps microorganisms intact/viable. Bacterial cells in the sample may be detected using Prussian blue formation by mixing the bacterial cells with a visualization buffer.

Below is described a lysis buffer for selectively lysing mammalian eukaryotic cells in a liquid sample, such as blood sample, a liquid food sample or liquidised food sample, or a beverage sample, comprising mammalian eukaryotic cells and possibly microorganisms, such as bacterial cells, archaea, fungi, protozoa, algae, virus particles, or combinations thereof. Below and in FIG. 1 is described a method for selectively lysing mammalian eukaryotic cells in a liquid sample comprising mammalian eukaryotic cells and possibly microorganisms using the lysis buffer. The lysis buffer comprises saponin and cholate in a concentration ratio (w/v) of 1:5 to 10:1. Saponin may be present in the lysis buffer in a concentration of 0.6-80% (w/v) and cholate may be present in the lysis buffer in a concentration of 1-40% (w/v).

In the method illustrated in FIG. 1, a liquid sample comprising mammalian eukaryotic cells and possibly microorganisms is provided 100 and the lysis buffer described above is added 101 to the liquid sample, such that a concentration of saponin and cholate in the formed mixture is 0.6-20% (w/v) and 1-8% (w/v), respectively. The mixture is incubated 102, thereby lysing mammalian eukaryotic cells in the mixture. The result is a complete, or almost complete, selective rupture of mammalian eukaryotic cells while keeping up to 100% of the microorganisms viable in the liquid sample up to 1 hour of lysis buffer exposure. There is further no clump formation, aggregation, of ruptured cells in the lysis buffer treated sample. The remainders of the ruptured blood cells in the treated sample may have a smaller size than the size of viable microorganisms, e.g. less than 0.45 μm if the microorganisms are bacterial cells.

Once the liquid sample has been treated with the lysis buffer and the mammalian eukaryotic cells killed off, the liquid sample and its possible content of viable microorganisms can be analysed in various downstream analyses, phenotypic or genotypic analyses. The viable microorganisms may be separated 103 from other components in the lysis buffer treated sample (such as remainders of ruptured mammalian eukaryotic cells) before such further analysis, and possibly also enriched. This separation 103 may take place for example through filtration, as illustrated in FIG. 1. The lysis buffer treated sample is passed through a filter having a pore size smaller than a diameter of for example bacterial cells, such that the bacterial cells are captured on/in the filter. Alternatively, the microorganisms may be separated from the other components of the liquid sample but kept in solution.

As illustrated in FIG. 1, the method may further comprise to visualize viable bacterial cells in/on a sample (in solution or in/on a filter). The sample is incubated 104 in a visualization buffer. In the case with a filter with captured bacterial cells therein/thereon, the filter is immersed in the visualization buffer during illumination for visualization of viable bacterial cells through formation of Prussian blue. The visualization buffer comprises ferric cyanide and ferric citrate dissolved in for example water or a solution such as PBS, wherein a concentration of ferric cyanide in the buffer is 0.5 mM to 4.5 mM and a concentration of ferric citrate is 2 mM to 9 mM. The formation of Prussian blue is coupled to bacterial cell metabolism through a photo-catalytic approach. Using simple visible light illumination 105, provided by an artificial light source, the iron molecules uncouple from the citrate, freeing it up for Prussian blue formation in the viable bacterial cells present in/on the sample, resulting in the appearance of an intense blue colour detectable with the bare eye. At the provided conditions, the ferric citrate does not spontaneously reduce to iron (II) citrate, preventing the formation of Prussian blue in the absence of bacterial cells. The presence of formed Prussian blue corresponds to presence of viable bacterial cells in/on the sample. The Prussian blue formation needs both viable bacterial cells and a light source, and thereby the exact onset of Prussian blue formation can be perfectly controlled.

By using a reference sample with known prokaryotic cell concentration or by comparing the Prussian blue intensity with a reference curve it may be possible to determine an approximate concentration of viable bacterial cells in a sample.

In a modification of the method illustrated in FIG. 1 bacterial antibiotic susceptibility testing can be made. The method comprises to provide a volume of a liquid sample comprising mammalian eukaryotic cells and possibly bacterial cells, dividing the volume of the liquid sample in a test volume and a reference volume, adding an antibiotic to the test volume and adding the lysis buffer described above to the reference volume and to the test volume, respectively, such that concentrations of saponin and cholate in the formed mixtures is 0.6-20% (w/v) and 1-8% (w/v), respectively, and incubating the mixtures, thereby lysing mammalian eukaryotic cells in the mixture. Thereafter bacterial cells are isolated from the respective mixtures in/on a test sample and in/on a reference sample, respectively, and the reference samples is incubated in the visualization buffer described above during illumination, and the test sample is incubated in the visualization buffer described above in presence of an antibiotic during illumination. The test and reference samples are illuminated, thereby allowing Prussian blue formation, wherein presence of Prussian blue correlates to presence of viable bacterial cells in/on the test and reference samples, respectively, and Prussian blue intensity from the test sample and the reference sample are compared. Such information can be useful for identifying which antibiotic to use when treating a bacterial blood infection, such as sepsis.

Since the method preserves microorganism integrity and activity, it also allows susceptibility testing and the detection of live bacterial cells. Susceptible bacterial cells die after incubation with the antibiotic and there is no colour development. On the contrary, resistant bacterial cells remain metabolically active and start the photo-catalytic cascade and the corresponding blue colour formation.

EXPERIMENTAL

The experiments discussed below are mostly related to using blood as the liquid sample. The results discussed can be transferred to other liquid solutions comprising mammalian eukaryotic cells and possibly microorganisms, such as urine, beverage, water, liquid or liquidized food sample

Effect of Lysis Buffer on Blood Cells

The effect of lysis buffer on the viability of whole blood cells was initially tested. In this case, 1 mL of whole blood was treated with 10 ml of lysis buffer mix (1:10 v/v ratio) and incubated for 5 min at room temperature with continuous stirring. The concentration of saponin and cholate in the mixture was here 1% (w/v) and 2 (w/v), respectively. After treatment, samples presented a less intense red colour and lower viscosity due to cell lysis. This was confirmed by optical microscopy, where blood cells clearly observed in untreated blood samples completely disappeared after 5 min exposure to lysis buffer. Even though, rupturing of blood cells happen instantaneously, 5 min of exposure time was given to make sure complete lysis of blood cells. (Viewed in a well using bright field microscope with 10× objective.)

It is worth mentioning that red blood cells (RBCs) represent the majority of cells in blood (about 45%) and were the responsible for most of the changes observed in the whole blood samples. Thus, to evaluate the effect of the lysis buffer on other blood cell fractions, they should be first isolated from whole blood and analysed independently. The effect of lysis buffer on White blood cells (WBCs) was studied in separate. To this end, standard ficoll-paque density gradient separation was performed on 10 ml of whole blood to separate blood cells from its components. Isolated WBCs and platelets were stained with calcein AM dye and anti-CD61 antibody respectively, for 15 min in the dark to avoid photo-bleaching of the fluorescent dye and incubated with the lysis buffer at room temperature. The effect of lysis buffer was evident by fluorescent microscopy, showing complete rupture of WBCs and platelets after 5 min of incubation.

Lysis of blood cells over time was tested. Whole blood was treated with the lysis buffer in 1:10 (v/v) ratio (1% Saponin and 2% Cholate) and bright field images were taken from 0 to 100 s to observe the lysis of blood cells on a well plate. At 0 s (whole blood), blood cells were clearly visible. After the addition of lysis buffer, minimum to no cells were visible after 100 s.

The effect of concentration of lysis buffer on whole blood was tested. Different volume to volume ratio of whole blood to lysis buffer from 1:1 to 1:10 was tested. The results showed that there was complete rupture of blood cells for all the combinations. Highest concentration of 1:10 was selected to ensure complete lysis of cells.

Effect of Lysis Buffer on Bacterial Viability

For a metabolic detection of living bacteria and future susceptibility testing, bacteria isolated from blood samples with the lysis buffer should keep viability and metabolic activity. To study the effect of the lysis buffer on bacteria, samples were lysed with the buffer, bacteria were captured in filters and analysed by OD after incubation in Luria-Bertani (LB) broth. In FIG. 2*a* and FIG. 2*b* is shown the effect of lysis buffer on viability of *E. coli* and Staph in separate experiments. OD values were measured for different conditions with two negative controls (with no bacteria), two positive controls (bacteria in lysate and bacteria in blood) and a sample (bacteria in blood and lysate) exposing the lysis buffer for 5, 30 and 60 min. Similar OD values for sample and positive control 1 show that the viability of bacteria can be retained up to 60 min of lysis buffer exposure.

Detection of Viable Bacteria Using Prussian Blue (PB)

Detection of viable bacteria is done on the filter paper by visualizing the Prussian blue colour formed on the filter paper by naked eye. The protocol used for detection method is shown in schematic of FIG. 1. Before performing blood based experiments, optimization of PB based bacterial detection was initially performed by spiking known concentration of bacteria in MH media and used as sample. After the sample containing bacteria is treated with lysis buffer and filtered, retained bacteria on the filter paper are incubated under constant illumination with the electrochromic precursors, i.e. 0.625 mM ferricyanide and 2.5 mM ferric ammonium citrate. Viable bacteria metabolically reduce iron (III) complexes, initiating a photo-catalytic cascade toward Prussian Blue formation over time. The combination of these precursors is referred collectively as PB solution as they form of Prussian blue colour in the presence of viable bacteria.

In FIG. 3 is shown Prussian blue based detection of *E. coli* spiked in Mueller-Hinton (MH) media on filter paper. (A) Graph showing the OD values of PB solution containing filter papers dipped after processing different samples, measured after of incubation at 600 nm and 720 nm. A significance difference in OD values was observed from negative controls 'MH' and 'MH+lysis buffer' when compared to samples containing *E. coli*. Similar OD values for samples '*E. coli*+MH' and '*E. coli*+Lysis buffer+MH' showed a very low influence of lysis buffer on the viability and formation of PB formation from bacteria. (B) Prussian blue colour was observed by naked eye on the filter paper that was processed with samples containing *E. coli* (n=3).

FIG. 4 shows time needed for bacteria detection using Prussian blue (PB) colour formation using different concentration of *E. coli* (10^8 to 10^2 CFU/mL) spiked in MH. The first PB colour formation on the filter paper was observed after 3 hr of incubation of filter paper in PB solution for higher concentration of *E. coli* (10^8 and 10^6 CFU/mL). With increase in time of incubation, the OD value increases (3, 5, 11 and 17 hr) due to the growth of bacteria. Between 3 to 5 hr is the minimum time needed to detect high concentration of bacteria using PB colour formation while lower concentration of bacteria can be detected between 5 to 11 hr.

FIG. 5 shows detection of *E. coli* spiked into whole blood. Known concentration of *E. coli* (1000 CFU/mL) was spiked into whole blood after incubating the filter paper for 17 hr in PB solution for all the samples. Similar OD values of the solution and PB colour formation on filter paper was observed for samples containing *E. coli* ('MH+*E. coli*' and 'Blood+*E. coli*+*Lysis*') dipped in PB solution. This colour formation indicates the viability of gram negative bacteria and can be detected from whole blood.

FIG. 6 shows detection of gram positive (*Staphylococcus Capitis*) bacteria in whole blood. Known concentration of Staph (1000 CFU/mL) was spiked into whole blood and OD value of the solution was measured (n=3). After 17 hr of incubation, the filter paper was removed and placed outside to observe the PB colour formation on the filter paper. Similar OD values of the solution and PB colour formation on filter paper was observed for samples containing Staph ('MH+Staph' and 'Blood+Staph+Lysis') dipped in PB solution. This colour formation indicates the viability of gram positive bacteria and can be detected from whole blood.

Antibiotic Susceptibility Testing

FIGS. 7 and 8 show antibiotic susceptibility testing. The lysis buffer based sample preparation method combined with detection using PB formation was used to perform antibiotic susceptibility testing (recommended by EUCAST [15]) using different concentration of ampicillin and gentamicin in separate experiments, on *E. coli* ATCC 25922 bacteria strain (106 CFU/mL) spiked in blood (sample) and in MH media (positive control). 'MH+Lysis buffer' is used as negative control (NC). It was observed that with increase in concentration of ampicillin (2 mg/L to 16 mg/L) and gentamicin (0.5 mg/L to 8 mg/L), the growth of bacteria decreased as shown as OD value measurement in the graph after 16 hr of incubation. The corresponding decrease in PB colour formation on the filter paper with increase in ampicillin and gentamicin concentration is shown on top of each bar in the graphs of the FIG. 7 and FIG. 8, respectively. The MIC of ampicillin and gentamicin was determined to be 16 and 8 mg/L respectively, which was in agreement with the MIC range provided by EUCAST for *E. coli* ATCC 25922.

REFERENCES

1. Javaloyas, M., D. Garcia-Somoza, and F. Gudiol, *Epidemiology and prognosis of bacteremia: A* 10-*y study in a community hospital*. Scandinavian Journal of Infectious Diseases, 2002. 34(6): p. 436-441.
2. Singer, M., et al., *The Third International Consensus Definitions for Sepsis and Septic Shock* (*Sepsis*-3). JAMA, 2016. 315(8): p. 801-10.
3. Yagupsky, P. and F. S. Nolte, *Quantitative Aspects of Septicemia*. Clinical Microbiology Reviews, 1990. 3(3): p. 269-279.
4. Kumar, A., et al., *Duration of hypotension before initiation of effective antimicrobial therapy is the critical determinant of survival in human septic shock*. Crit Care Med, 2006. 34(6): p. 1589-96.
5. Frank, U., et al., *Controlled clinical comparison of three commercial blood culture systems*. European Journal of Clinical Microbiology & Infectious Diseases, 1999. 18(4): p. 248-255.
6. Garcia-Prats, J. A., et al., *Rapid detection of microorganisms in blood cultures of newborn infants utilizing an automated blood culture system*. Pediatrics, 2000. 105(3 Pt 1): p. 523-7.
7. Haimi-Cohen, Y., E. M. Vellozzi, and L. G. Rubin, *Initial concentration of Staphylococcus epidermidis in simulated pediatric blood cultures correlates with time to positive results with the automated, continuously monitored BACTEC blood culture system*. J Clin Microbiol, 2002. 40(3): p. 898-901.
8. Sinha, M., et al., *Emerging Technologies for Molecular Diagnosis of Sepsis*. Clinical Microbiology Reviews, 2018. 31(2).
9. Hosokawa, M., et al., *Leukocyte counting from a small amount of whole blood using a size-controlled microcavity array*. Biotechnology and Bioengineering, 2012. 109 (8): p. 2017-2024.
10. Barr, I. G., A. Sjolander, and J. C. Cox, *ISCOMs and other saponin based adjuvants*. Advanced Drug Delivery Reviews, 1998. 32(3): p. 247-271.
11. Zhao, X. M., et al., *Dioscin, a natural steroid saponin, shows remarkable protective effect against acetaminophen-induced liver damage in vitro and in vivo*. Toxicology Letters, 2012. 214(1): p. 69-80.
12. Schubert, R., et al., *Structural-Changes in Membranes of Large Unilamellar Vesicles after Binding of Sodium Cholate*. Biochemistry, 1986. 25(18): p. 5263-5269.
13. Albalak, A., et al., *Effects of submicellar bile salt concentrations on biological membrane permeability to low molecular weight non-ionic solutes*. Biochemistry, 1996. 35(24): p. 7936-7945.
14. Ravnikar, M., et al., *Chemoporation using saponins or cholates: an alternative method for transformation of bacterial cells*. Biotechnology Letters, 2009. 31(12): p. 1943-1946. *nsor for monitoring and detecting acute toxicity in water*. Analyst, 2013. 138(2): p. 702-707.
15. EUCAST, 2020. *The European Committee on Antimicrobial Susceptibility Testing. Outline and extended internal quality control for MIC determination and disk diffusion as recommended by EUCAST*. Version 10.0, https://www.eucast.org/.

What is claimed is:

1. A method of selectively lysing mammalian eukaryotic cells in a liquid sample comprising mammalian eukaryotic cells and possibly microorganisms, comprising:

adding to a volume of the liquid sample comprising the mammalian eukaryotic cells and possibly the microorganisms a lysis buffer comprising saponin and cholate in a concentration ratio (w/v) of 1:5 to 10:1 such that a concentration of saponin and cholate in a formed mixture is 0.6-20% (w/v) and 1-8% (w/v), respectively, incubating the formed mixture, thereby lysing the mammalian eukaryotic cells in the formed mixture.

2. A method of separating and enriching microorganisms, the method comprising the method of claim 1 and further comprising, after the incubation, separating microorganisms from other components in a volume of the liquid sample and enriching the microorganisms.

3. The method of claim 1, further comprising visualizing viable bacterial cells in the sample.

4. The method of claim 1, wherein the liquid sample is selected from the group consisting of a blood sample, urine, beverage, water, and liquidized food sample.

5. The method of claim 1, wherein saponin is present in the lysis buffer in a concentration of 0.6-80% (w/v) and cholate is present in the lysis buffer in a concentration of 1-40% (w/v).

6. A method for bacterial antibiotic susceptibility testing, the method comprising:

dividing a volume of a liquid sample comprising mammalian eukaryotic cells and possibly bacterial cells in a test volume and a reference volume, adding a lysis buffer comprising saponin and cholate in a concentration ratio (w/v) of 1:5 to 10:1 to the reference volume and to the test volume, respectively, such that a concentration of saponin and cholate in formed mixtures is 0.6-20% (w/v) and 1-8% (w/v), respectively, incubating the formed mixtures, thereby lysing mammalian eukaryotic cells in the formed mixtures, isolating bacterial cells from the respective mixtures in/on a test sample and in/on a reference sample, respectively, incubating the reference sample in a visualization buffer during illumination, and incubating the test sample in the visualization buffer in presence of an antibiotic during illumination, thereby allowing Prussian blue formation, wherein presence of Prussian blue correlates to presence of viable bacterial cells in/on the test sample and in/on the reference sample, respectively, comparing Prussian blue intensity from the test sample and the reference sample, wherein the visualization buffer comprises ferric cyanide and/or ferrocyanide and ferric citrate, wherein a concentration of ferric cyanide and/or ferrocyanide in the visualization buffer is 0.5 mM to 4.5 mM and a concentration of ferric citrate is 2 mM to 9 mM.

* * * * *